US011045604B2

(12) United States Patent
Ottolino et al.

(10) Patent No.: US 11,045,604 B2
(45) Date of Patent: Jun. 29, 2021

(54) MEDICAL DEVICE ASSEMBLY

(71) Applicant: William Beaumont Hospital, Royal Oak, MI (US)

(72) Inventors: Rocco Ottolino, Berkley, MI (US); Gregory Megahan, Rochester Hills, MI (US); Kenneth Peters, Huntington Woods, MI (US); Donna J. Carrico, Suttons Bay, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 558 days.

(21) Appl. No.: 15/673,997

(22) Filed: Aug. 10, 2017

(65) Prior Publication Data

US 2018/0043098 A1  Feb. 15, 2018

Related U.S. Application Data

(60) Provisional application No. 62/373,574, filed on Aug. 11, 2016.

(51) Int. Cl.
*A61M 5/31* (2006.01)
*A61B 5/00* (2006.01)
*A61B 5/389* (2021.01)

(52) U.S. Cl.
CPC .............. *A61M 5/31* (2013.01); *A61B 5/389* (2021.01); *A61B 5/4824* (2013.01); *A61B 2562/0247* (2013.01); *A61B 2562/0261* (2013.01); *A61M 2205/0244* (2013.01); *A61M 2205/332* (2013.01); *A61M 2205/50* (2013.01); *A61M 2205/587* (2013.01); *A61M 2205/8206* (2013.01)

(58) Field of Classification Search
CPC .............. A61M 5/31; A61M 2205/332; A61M 2205/0244; A61B 5/4824; A61B 5/0488; A61B 2562/0247; A61B 2562/0261
USPC ........................................................ 604/503
See application file for complete search history.

(56) References Cited

U.S. PATENT DOCUMENTS

| 4,928,707 | A | | 5/1990 | Schiffman et al. |
| 5,533,514 | A | * | 7/1996 | Lavigne ............... A61B 5/0053 600/553 |
| 5,592,947 | A | * | 1/1997 | Lavigne ............... A61B 5/0053 600/557 |
| 6,306,101 | B1 | | 10/2001 | Vaynovsky et al. |
| 8,224,464 | B2 | | 7/2012 | Wise |
| 8,337,435 | B2 | | 12/2012 | Wise |
| 8,632,482 | B2 | | 1/2014 | Wise |

(Continued)

*Primary Examiner* — Brandy S Lee
*Assistant Examiner* — Nidah H Hussain
(74) *Attorney, Agent, or Firm* — Honigman LLP; Douglas H. Siegel; Jonathan P. O'Brien

(57) ABSTRACT

A medical device assembly is disclosed. The medical device assembly includes a therapeusis delivery portion and an algometer portion. The therapeusis delivery portion includes a body having a proximal end and a distal end. The algometer portion includes a body having a proximal end and a distal end. The body of the therapeusis delivery portion defines a therapeusis-delivering passage and an algometer-receiving passage. The algometer-receiving passage may be sized to receive a portion of the algometer portion for connecting the algometer portion to the therapeusis delivery portion. A portion of medical device assembly is also disclosed. A method is also disclosed.

26 Claims, 13 Drawing Sheets

(56) References Cited

U.S. PATENT DOCUMENTS

| | | |
|---|---|---|
| 8,639,360 B2 | 1/2014 | Wise |
| 2010/0132058 A1 | 5/2010 | Diatchenko et al. |
| 2011/0144541 A1* | 6/2011 | Kuroda ................ A61B 5/0053 600/587 |
| 2013/0244233 A1 | 9/2013 | Diatchenko et al. |
| 2014/0073999 A1 | 3/2014 | Wise |
| 2014/0088469 A1 | 3/2014 | Wise |
| 2014/0275846 A1* | 9/2014 | Fitzgerald ............ A61B 5/0053 600/301 |
| 2014/0276549 A1* | 9/2014 | Osorio ................ A61B 5/0205 604/503 |
| 2015/0127077 A1 | 5/2015 | Asher et al. |
| 2017/0087364 A1* | 3/2017 | Cartledge ............ A61N 1/3603 |

* cited by examiner

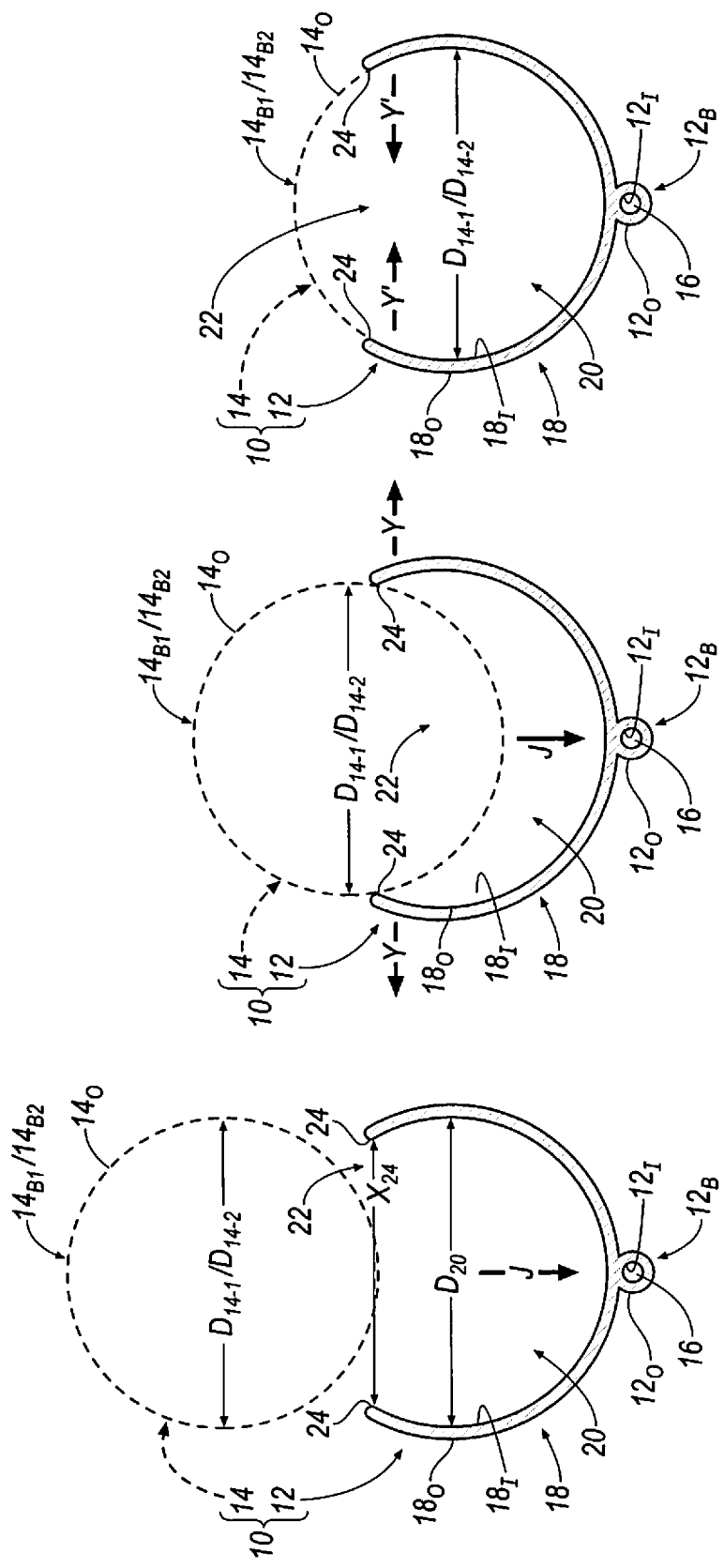

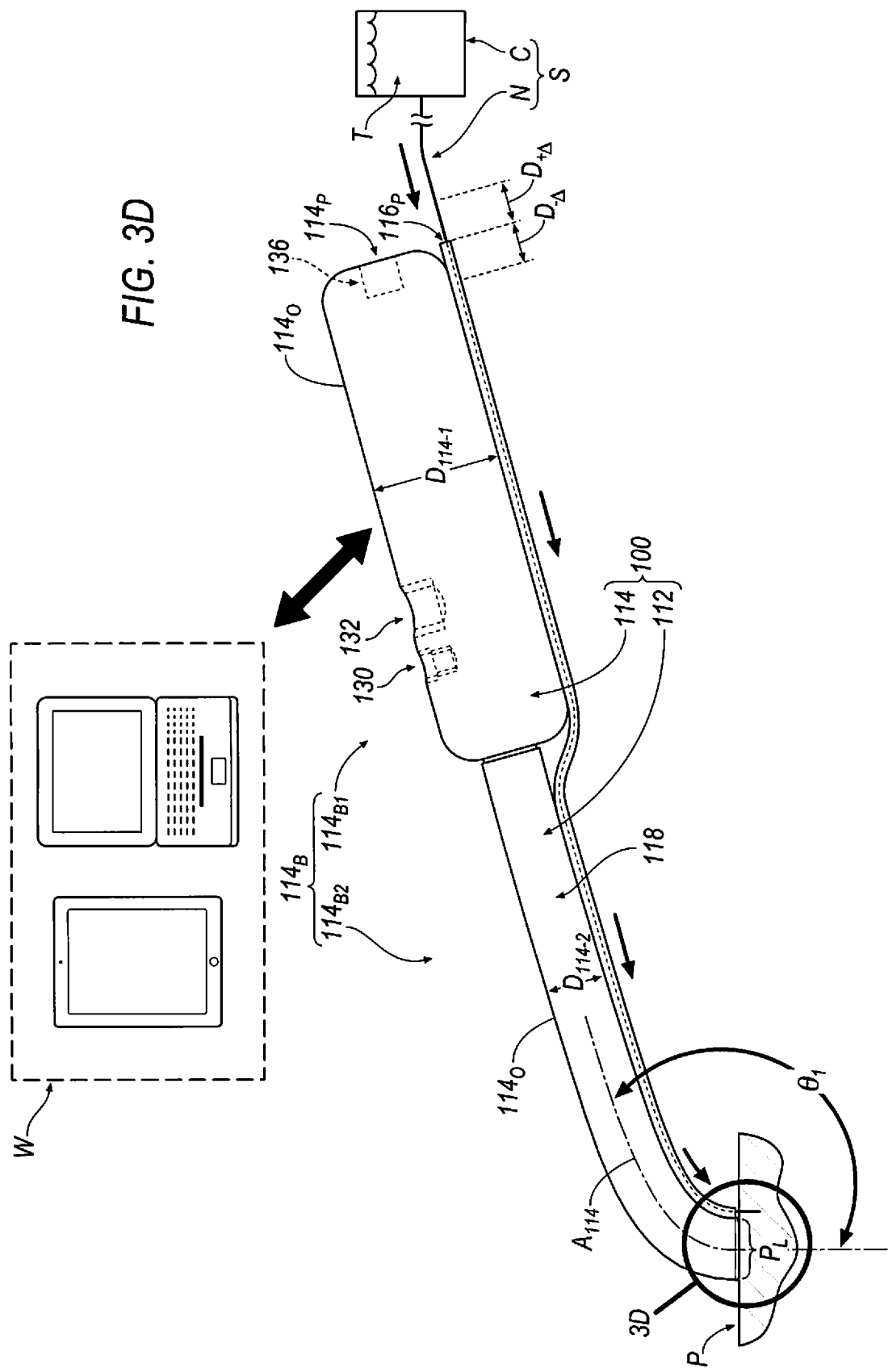

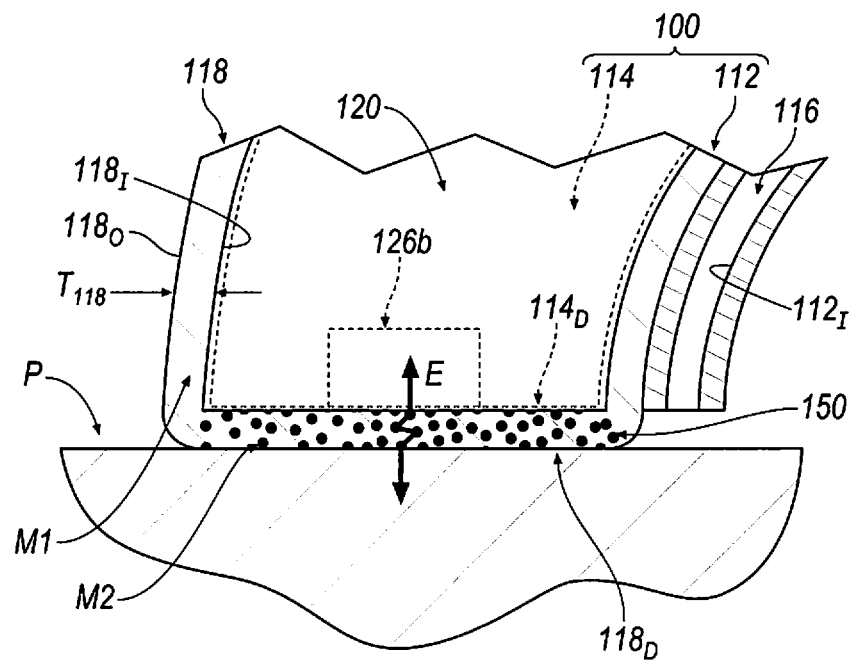
FIG. 3D'
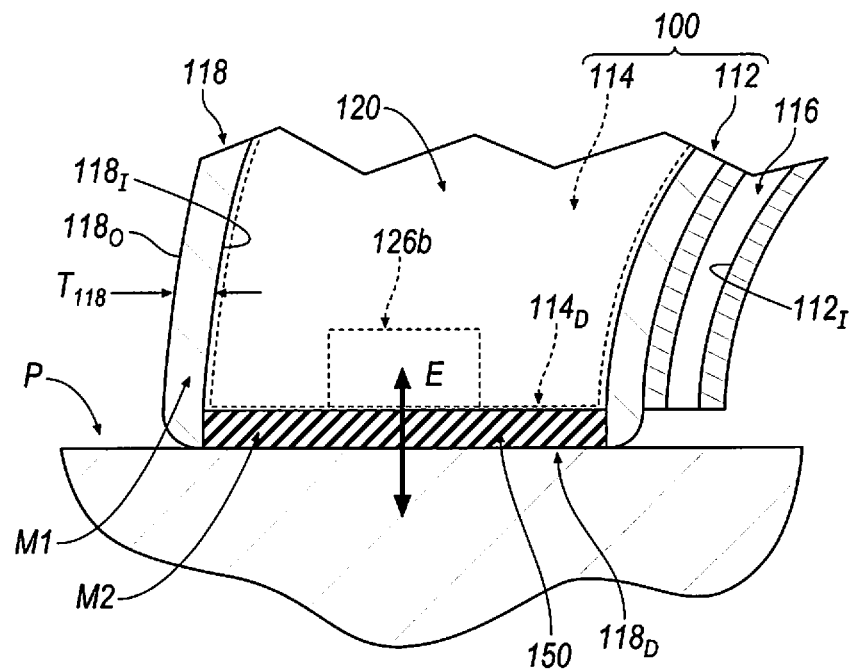
FIG. 3D"

MEDICAL DEVICE ASSEMBLY

CROSS REFERENCE TO RELATED APPLICATION

This U.S. patent application claims priority U.S. Provisional Patent Application 62/373,574, filed on Aug. 11, 2016, which is hereby incorporated by reference in its entirety.

TECHNICAL FIELD

This disclosure relates to a medical device assembly.

BACKGROUND

Various medical devices for determining a pain threshold of a patient are known in the art, such as, for example, algometers; an algometer is used to measure the pressure and/or force eliciting a pressure-pain threshold. While known medical devices have proven to be acceptable for such applications, such conventional medical devices are nevertheless susceptible to improvements that may enhance their overall performance and cost. Therefore, a need exists to develop improved medical devices and methodologies for utilizing the same that advance the art.

SUMMARY

One aspect of the disclosure provides a medical device assembly. The medical device assembly includes a therapeusis delivery portion and an algometer portion. The therapeusis delivery portion includes a body having a proximal end and a distal end. The algometer portion includes a body having a proximal end and a distal end. The body of the therapeusis delivery portion defines a therapeusis-delivering passage and an algometer-receiving passage. The algometer-receiving passage may be sized to receive a portion of the algometer portion for connecting the algometer portion to the therapeusis delivery portion.

Implementations of the disclosure may include one or more of the following optional features. In some implementations, the algometer portion includes a handle portion and a wand portion. In some implementations, the algometer-receiving passage may be defined by one or more attachment clips. The one or more attachment clips includes a plurality of attachment clips. At least a first attachment clip of the plurality of attachment clips may be sized to connect to the handle portion of the algometer portion. At least a second attachment clip of the plurality of attachment clips may be sized to connect to the wand portion of the algometer portion.

In some instances, the body of the therapeusis delivery portion may be defined by a substantially tube shape. An inner surface of the body of the therapeusis delivery portion defines the therapeusis-delivering passage.

In some examples, the body of the therapeusis delivery portion includes a sheath. The sheath includes an inner surface and an outer surface. The inner surface of the sheath defines the algometer-receiving passage.

In some implementations, the sheath includes a proximal opening and an enclosed distal end. The proximal opening permits fluid communication with the algometer-receiving passage.

In some instances, the body of the therapeusis delivery portion may be defined by a substantially tube shape. An inner surface of the body of the therapeusis delivery portion defines the therapeusis-delivering passage.

In some examples, at least a portion of the enclosed distal end of the sheath includes an electrically-conductive material. In another example, all of a thickness of the enclosed distal end of the sheath may be formed from the electrically-conductive material.

In yet another example, a thickness of the enclosed distal end of the sheath may be formed from a first material and a second material. The first material may be a non-conductive material. The second material may be the electrically-conductive material. The electrically-conductive material may be impregnated within the non-conductive material.

In some implementations, a thickness of the enclosed distal end of the sheath may be bound by the inner surface of the sheath and the outer surface of the sheath. The conductive material may be disposed adjacent the outer surface of the sheath along the enclosed distal end of the sheath.

In some instances, the medical device further includes one or more sensors and a processor. The one or more sensors may be connected to the distal end of the algometer portion. The processor may be communicatively-coupled to the one or more sensors. The processor may be disposed within the body of the algometer portion. The one or more sensors may include a force application sensor. The one or more sensors may include an electromyography (EMG) sensor.

In some examples, the medical device further includes one or more visual indicators and one or more user input devices. The one or more visual indicators may be attached to the body of the algometer portion. The one or more visual indicators may include at least one of a light emitting diode and a liquid crystal display. The one or more user input devices may be attached to the body of the algometer portion.

Another aspect of the disclosure provides a portion of medical device assembly. The portion of medical device assembly includes a therapeusis delivery portion. The therapeusis delivery portion includes a body having a proximal end and a distal end. The body of the therapeusis delivery portion may define a therapeusis-delivering passage and an algometer-receiving passage that may be sized to receive a portion of an algometer portion of the medical device assembly, thereby connecting the algometer portion to the therapeusis delivery portion and forming the medical device assembly. The body of the therapeusis delivery portion includes a sheath. The sheath includes an inner surface and an outer surface. The inner surface of the sheath may define the algometer-receiving passage.

Implementations of the disclosure may include one or more of the following optional features. In some implementations, the sheath includes a proximal opening and an enclosed distal end. The proximal opening permits fluid communication with the algometer-receiving passage.

In some implementations, at least a portion of the enclosed distal end of the sheath may include an electrically-conductive material. In other implementations, all of a thickness of the enclosed distal end of the sheath may be formed from the electrically-conductive material.

In other implementations, a thickness of the enclosed distal end of the sheath may be formed from a first material and a second material. The first material may be a non-conductive material. The second material may be the electrically-conductive material. The electrically-conductive material may be impregnated within the non-conductive material.

In some instances, a thickness of the enclosed distal end of the sheath may be bound by the inner surface of the sheath and the outer surface of the sheath. The conductive material may be disposed adjacent the outer surface of the sheath along the enclosed distal end of the sheath.

In yet another aspect of the disclosure provides a method. The method includes disposing a force application sensor of an algometer portion of a medical device assembly adjacent a locus of a patient; determining a level of pain being experienced by the patient; and providing therapy to the locus of the patient by communicating therapeusis from a therapeusis container through a needle and to the locus.

Implementations of the disclosure may include one or more of the following optional features. In some implementations, prior to the disposing step, the method includes: assembling the medical device by connecting a therapeusis delivery portion to an algometer portion. The therapeusis delivery portion may include a body. The algometer portion may include a body having a proximal end and a distal end. The body of the therapeusis delivery portion may define a therapeusis-delivering passage. A portion of the algometer portion is disposed within the algometer-receiving passage for assembling the medical device.

In some implementations, the method further includes disposing one or more sensors connected to the distal end of the algometer portion adjacent the locus of the patient; and obtaining data from the one or more sensors. The method may further include obtaining an amount of force applied to the locus of the patient. The method may further include obtaining a measurement related to changes in nerve conduction or muscle spasms at or near the locus of the patient.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2A is a cross-sectional view of the medical device assembly according to line 2A-2A of FIG. 1A.

FIG. 2B is a partially assembled view of the medical device assembly according to FIG. 2A.

FIG. 2C is a partially assembled view of the medical device assembly according to FIG. 2B and line 2C-2C of FIG. 1B.

FIG. 3D' is an exemplary enlarged view of FIG. 3D according to line 3D.

FIG. 3D'' is an exemplary enlarged view of FIG. 3D according to line 3D.

FIG. 3D''' is an exemplary enlarged view of FIG. 3D according to line 3D.

Like reference symbols in the various drawings indicate like elements.

DETAILED DESCRIPTION

Figure 1A:
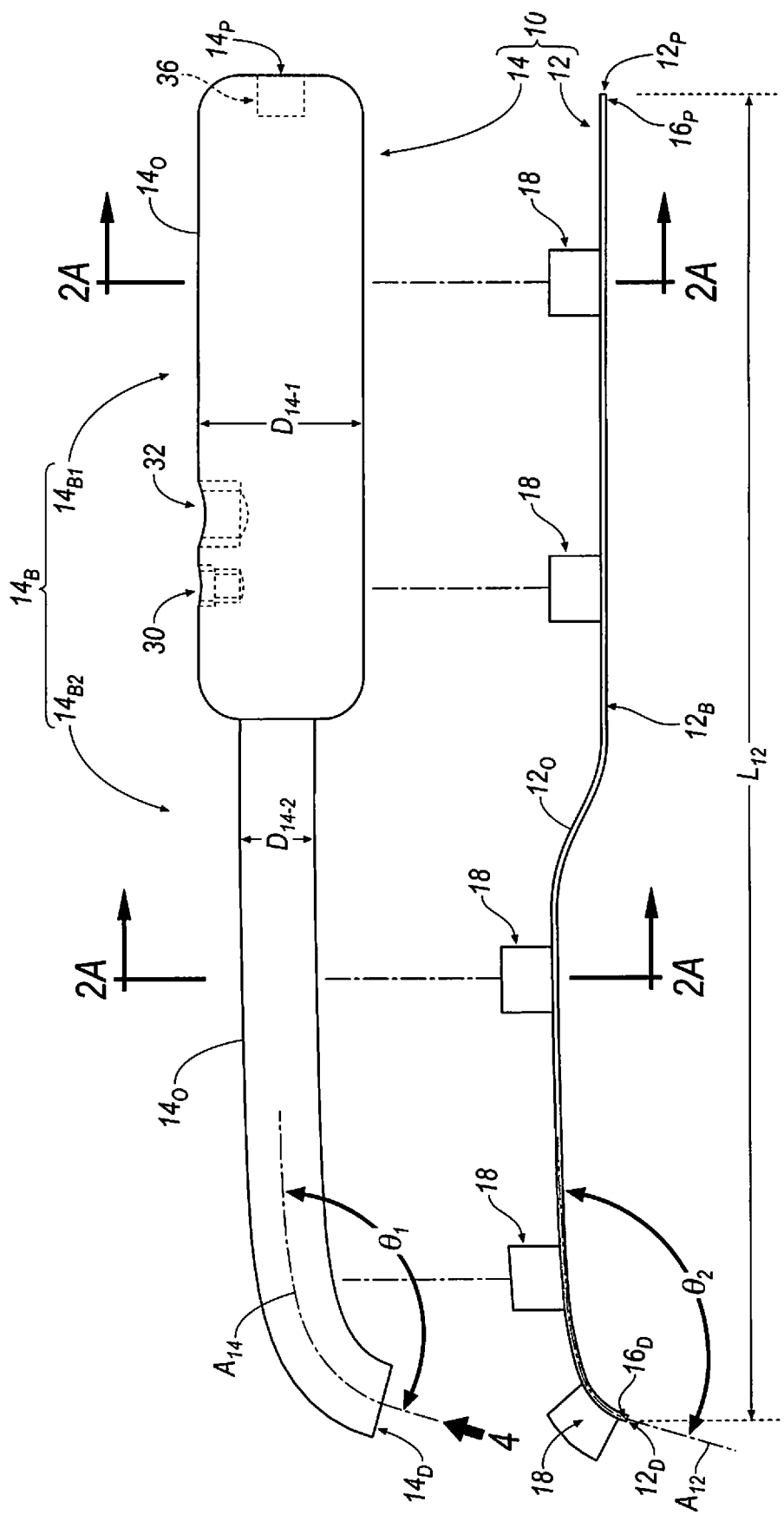
FIG. 1A is an exploded side view of an exemplary medical device assembly.

Referring to FIGS. 1A-ID, an exemplary medical device assembly is shown generally at 10. The medical device assembly 10 includes a therapeusis delivery portion 12 (see also, FIGS. 2A-2C) and an algometer portion 14. Each of the therapeusis delivery portion 12 and the algometer portion 14 includes a body $12_B$, $14_B$ having a proximal end $12_P$, $14_P$ and a distal end $12_D$, $14_D$.

The body $12_B$ of the therapeusis delivery portion 12 may form a tube-shaped body having a therapeusis-delivering passage 16 (see, e.g., FIGS. 2A-2C) extending therethrough. The tube-shaped body $12_B$ of the therapeusis delivery portion 12 may include one or more attachment clips 18 integrally extending from or attached to an outer surface $12_O$ of the tube-shaped body $12_B$ of the therapeusis delivery portion 12. An inner surface $12_I$ (see, e.g., FIGS. 2A-2C) of the tube-shaped body $12_B$ defines the therapeusis-delivering passage 16.

The body $14_B$ of the algometer portion 14 includes a handle portion $14_{B1}$ and a wand portion $14_{B2}$. The handle portion $14_{B1}$ includes the proximal end $14_P$ of the algometer portion 14 and the wand portion $14_{B2}$ includes the distal end $14_D$ of the algometer portion 14. The handle portion $14_{B1}$ and the wand portion $14_{B2}$ may be respectively defined by a diameter $D_{14-1}$, $D_{14-2}$; the diameter $D_{14-1}$ of the handle portion $14_{B1}$ may be greater than the diameter $D_{14-2}$ of the wand portion $14_{B2}$.

As seen in FIGS. 2A-2C, each attachment clip 18 of the one or more attachment clips 18 may be defined by a substantially C-shaped body having an inner surface $18_I$ and an outer surface $18_O$. The inner surface $18_I$ of each attachment clip 18 defines an axial algometer-receiving passage 20. The axial algometer-receiving passage 20 may be defined by a diameter $D_{20}$ (see, e.g. FIG. 2A). Access to the axial algometer-receiving passage 20 is permitting by a radial opening 22 defined by opposing ends 24 of each attachment clip 18.

Figure 1B:
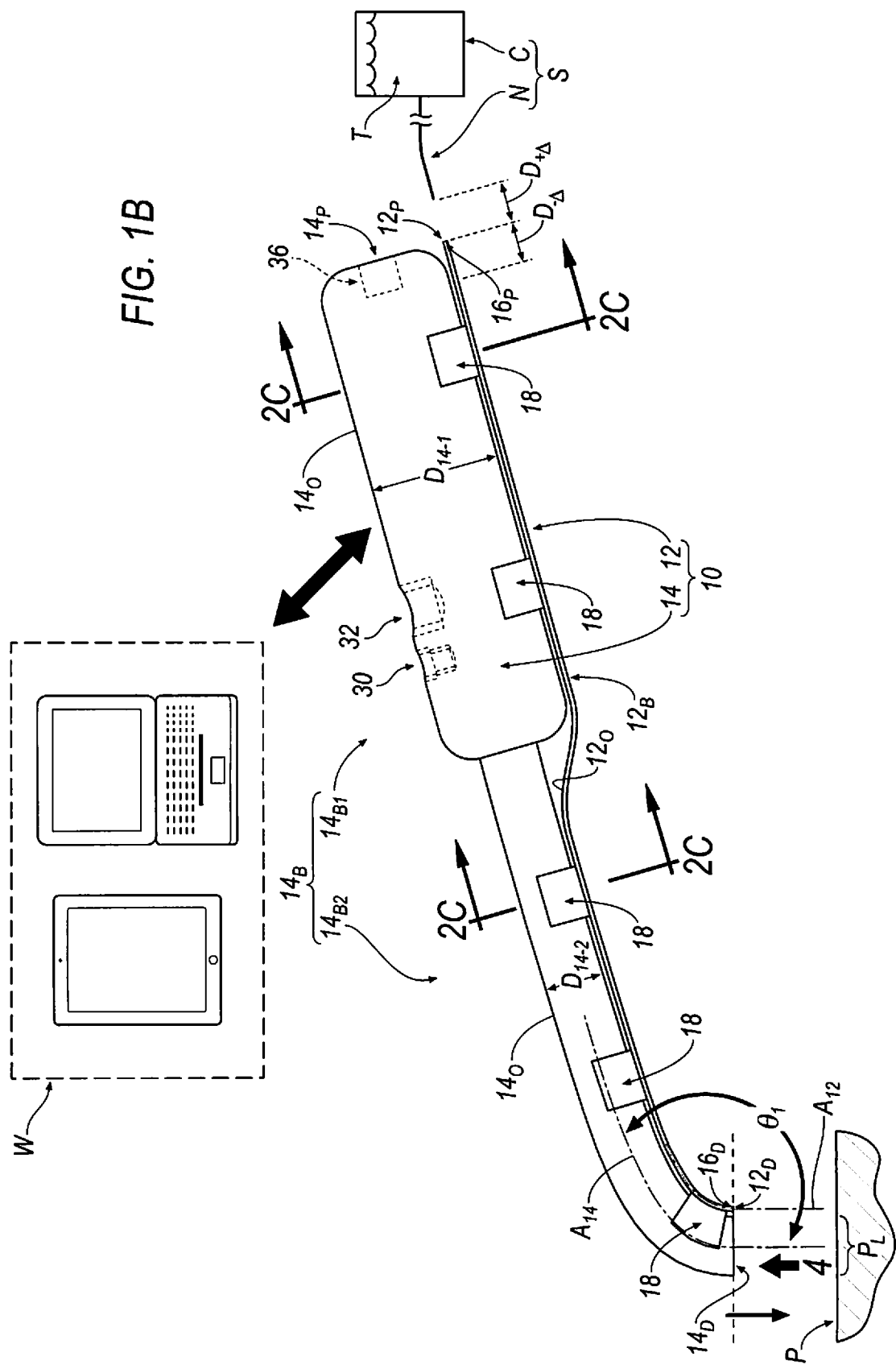
FIG. 1B is an assembled side view of the exemplary medical device assembly of FIG. 1A.

As seen in FIG. 2A, a non-radially-outwardly flexed, at-rest distance $X_{24}$ extending between the opposing ends 24 of each attachment clip 18 is sized to be less than the diameter $D_{14-1}$, $D_{14-2}$ of each of the handle portion $14_{B1}$ and the wand portion $14_{B2}$. The non-radially-outwardly flexed, at-rest distance $X_{24}$ is less than the diameter $D_{14-2}$ for any attachment clip 18 associated with the wand portion $14_{B2}$, and, correspondingly, the non-radially-outwardly flexed, at-rest distance $X_{24}$ is less than the diameter $D_{14-1}$ for any attachment clip 18 associated with the handle portion $14_{B1}$. With reference to FIG. 2B, as the one or more attachment clips 18 are brought into engagement with one or both of the handle portion $14_{B1}$ and the wand portion $14_{B2}$ of the body $14_B$ of the algometer portion 14 for the purpose of joining the therapeusis delivery portion 12 to the algometer portion 14, because the distance $X_{24}$ is sized to be less than the diameter $D_{14-1}$, $D_{14-2}$ of each of the handle portion $14_{B1}$ and the wand portion $14_{B2}$, the one or more attachment clips 18 are flexed radially outwardly (according to the direction of arrow Y) as the one or more attachment clips 18 are progressively joined (see, e.g., arrow J in FIGS. 2A-2B) to the body $14_B$ of the algometer portion 14. As seen in FIGS. 1B and 2C, upon the opposing ends 24 of each attachment clip 18 being advanced in the direction of arrow J along one or more of the handle portion $14_{B1}$ and the wand portion $14_{B2}$, the one or more attachment clips 18 are flexed radially inwardly (according to the direction of arrow Y') such that the inner surface $18_I$ of the one or more attachment clips 18 is disposed against and grips an outer surface $14_O$ of the body $14_B$ of the algometer portion 14 for joining the therapeusis delivery portion 12 to the algometer portion 14. After arranging the one or more attachment clips 18 adjacent to the outer surface $14_O$ of the body $14_B$ of the algometer portion 14, the tube-shaped body $12_B$ of the therapeusis delivery portion 12 is connected to the body $14_B$ algometer portion 14 for forming the medical device assembly 10.

Figure 1C:
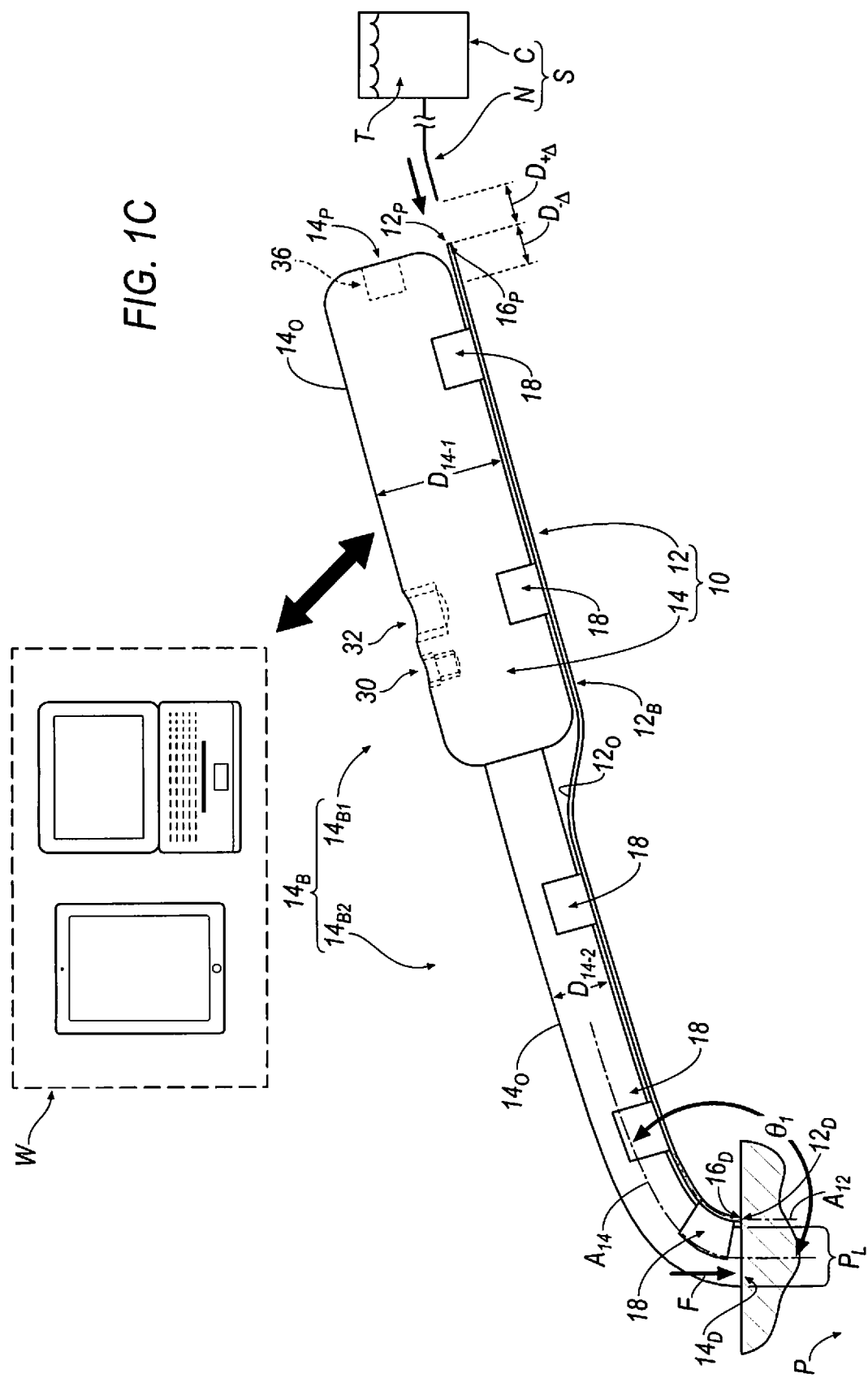
FIG. 1C is a side view of the medical device assembly of FIG. 1B disposed adjacent a patient.
Figure 1D:
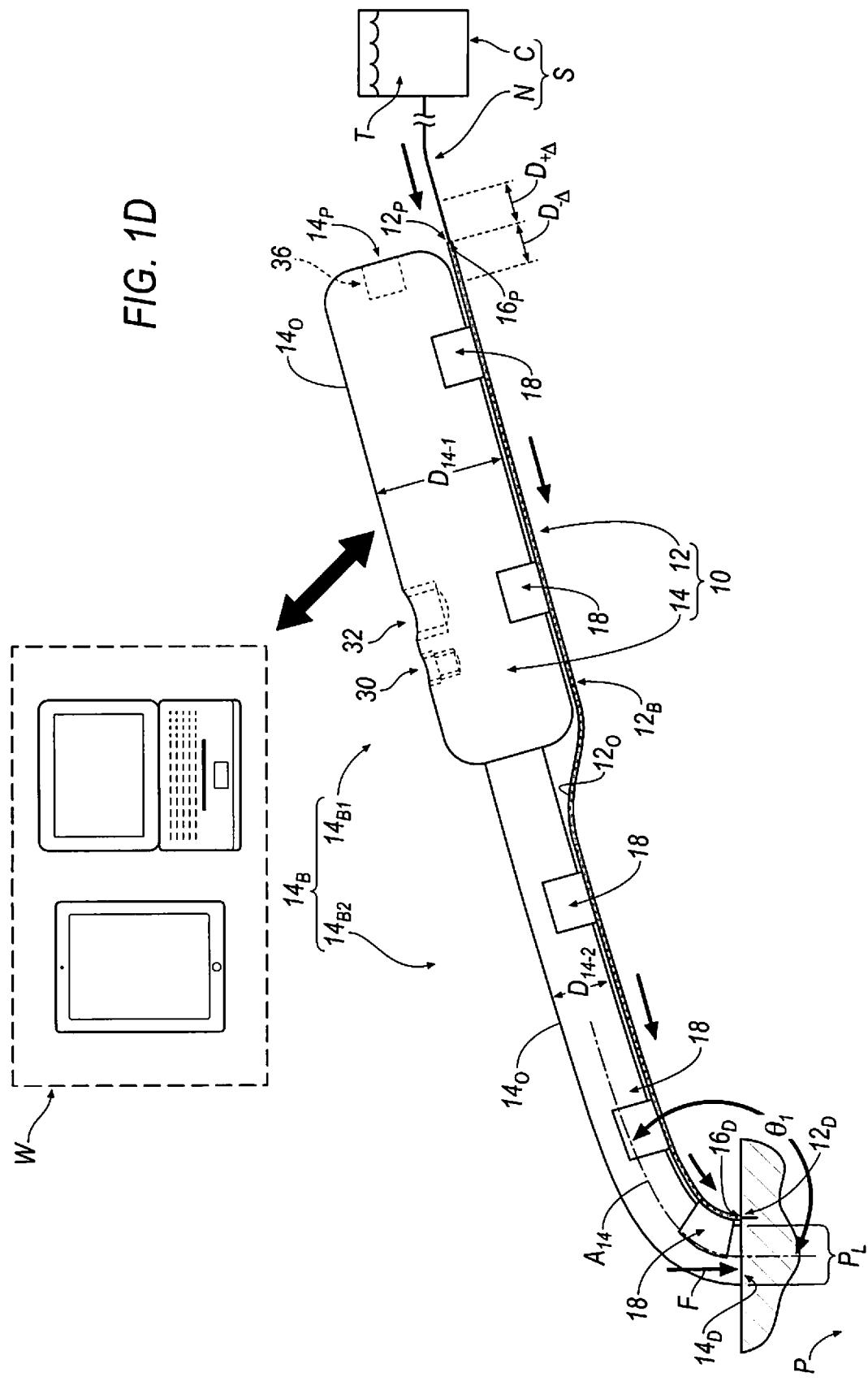
FIG. 1D is a side view of the medical device assembly of FIG. 1C showing therapeusis delivered to the patient by way of a needle extending through the medical device assembly that is interfaced with the patient.

As seen in FIGS. 1C-1D, the tube-shaped body $12_B$ of the therapeusis delivery portion 12 may define a therapeusis delivery port for delivering therapeusis T to a patient P. In order to deliver therapeusis T to the patient P, a flexible needle N may be reciprocatingly-disposed within the therapeusis-delivering passage 16 extending through the body $12_B$ of the therapeusis delivery portion 12. The flexible needle N is interfaced with the patient P by: (1) inserting the flexible needle N through the a proximal opening $16_P$ formed by the tube-shaped body $12_B$ of the therapeusis delivery portion 12 that is in fluid communication with the therapeusis-delivering passage 16, (2) extending the flexible needle N through the therapeusis-delivering passage 16 that extends along a length $L_{12}$ of the tube-shaped body $12_B$ of the therapeusis delivery portion 12 and (3) extending the flexible needle N out of a distal opening $16_D$ formed by the tube-shaped body $12_B$ of the therapeusis delivery portion 12 that is in fluid communication with the therapeusis-delivering passage 16. The flexible needle N may be connected to a therapeusis container C that contains the therapeusis T.

In some implementations, the flexible needle N and therapeusis container C may be a conventional syringe S. In an example, one or more of the flexible needle N and the therapeusis container C may be directly interfaced with the medical device assembly 10. In other example, one or more of the flexible needled N and the therapeusis container C may not be directly interfaced (i.e., one or more of the flexible needle N and the therapeusis container may be 'indirectly' interfaced) with the medical device assembly 10 in, for example, a free-floating arrangement such that an operator holds, for example, one or both of the therapeusis delivery portion 12 and the algometer portion 14 with one hand and then the operator operates/holds flexible needle N and/or the therapeusis container C with his/her other hand. In an example, if the flexible needle N and the therapeusis container C form a syringe S, the syringe S may be interfaced with the therapeusis delivery portion 12 by way of, for example, a threaded connection (by way of, e.g., a Luer lock, not shown).

Figure 4:
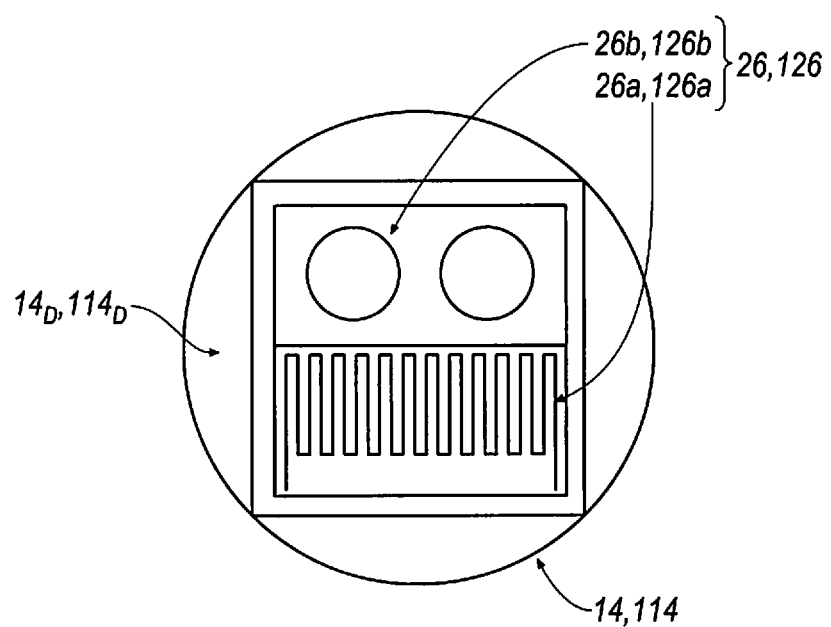
FIG. 4 is an end view of a portion of the medical device assembly according to arrow 4 of FIG. 1A or FIG. 3A.

With reference to FIG. 4, in an example, one or more sensors 26 may be connected to the distal end $14_D$ of the algometer portion 14. A sensor 26a of the one or more sensors 26 may include a force application sensor for measuring an amount of force (according to the direction of arrow F as seen in, e.g., FIGS. 1C-1D) imparted by an operator from the handle portion $14_{B1}$ of the $14_B$ to the distal end $14_D$ of the algometer portion 14. Another sensor 26b of the one or more sensors 26 may include a sensor that measures changes in nerve conduction or muscle spasms (e.g., an electromyography (EMG) sensor).

Prior to interfacing the flexible needle N with the medical device assembly 10 as seen in FIG. 1D, an operator disposes the force application sensor 26a adjacent a locus (e.g., a trigger-point) $P_L$ of a patient P (e.g., the levator ani muscles of the patient P) and applies an amount of force F thereto as seen in FIG. 1C. During the course of applying the force application sensor 26a adjacent the locus $P_L$ of the levator ani muscles of the patient P, the operator may ask the patient P to describe the level of pain being experienced (e.g., on a zero-to-ten threshold with zero being no pain being experienced and ten being an extreme amount of pain being experienced). With reference to FIG. 1D, if, for example, the operator determines that the level of pain being described by the patient P is sufficient for providing the therapeusis T to the locus $P_L$, the operator may then selectively interface the flexible needle N with the medical device assembly 10 as described above for communicating the therapeusis T: (1) from the therapeusis container C, (2) through the flexible needle N, and (3) to or near the site of the locus $P_L$ where the patient P has described the level of pain being experienced.

With reference to FIG. 1A, at least a first portion of the body $14_B$ of the algometer portion 14 may axially extend along a first axis $A_{14}$-$A_{14}$, and, in some instances, the tube-shaped body $12_B$ of the therapeusis delivery portion 12 may axially extend along a second axis $A_{12}$-$A_{12}$; the first axis $A_{14}$-$A_{14}$ and the second axis $A_{12}$-$A_{12}$ may be parallel to one another. With reference to FIG. 1B, after the therapeusis delivery portion 12 is attached to the algometer portion 14 as described above at FIGS. 2A-2C, in some instances, the distal end $12_D$ of the tube-shaped body $12_B$ of the therapeusis delivery portion 12 may be aligned with the distal end $14_D$ of the body $14_B$ of the algometer portion 14. Further, the proximal end $12_P$ of the tube-shaped body $12_B$ of the therapeusis delivery portion 12 may be arranged upstream of and extend beyond the proximal end $14_P$ of the body $14_B$ of the algometer portion 14 at a distance $D_{+A}$. Alternatively, the proximal end $12_P$ of the tube-shaped body $12_B$ of the therapeusis delivery portion 12 may be arranged downstream of the proximal end $14_P$ of the body 14a of the algometer portion 14 at a distance $D_{-A}$ (see, e.g., FIG. 1B). In some embodiments, the proximal end $12_P$ is arranged downstream of the handle portion $14_{B1}$ of the algometer portion $14_{B2}$ (i.e., $D_{-A}$ is equal to or shorter than the handle portion $14_{B1}$).

As seen in FIGS. 1A-1D, in some instances, both of the first axis $A_{14}$-$A_{14}$ and the second axis $A_{12}$-$A_{12}$ may define a non-linear axial component. For example, a second portion of the body $14_B$ of the algometer portion 14 proximate the distal end $14_D$ of the body $14_B$ of the algometer portion 14 may axially deviate along an arcuate path to define a non-linear axial component of the first axis $A_{14}$-$A_{14}$; as a result of the non-linearity of the first axis $A_{14}$-$A_{14}$, the body $14_B$ of the algometer portion 14 may be defined to curve at a first angle $\theta_1$. Similarly, as seen in FIGS. 1A-1D, the tube-shaped body $12_B$ of the therapeusis delivery portion 12 proximate the distal end $12_D$ may axially deviate along an arcuate path to define a non-linear axial component of the second axis $A_{12}$-$A_{12}$; as a result of the non-linearity of the second axis $A_{12}$-$A_{12}$, the tube-shaped body $12_B$ of the therapeusis delivery portion 12 may be defined to curve at a second angle $\theta_2$. Each of the first angle $\theta_1$ and the second angle $\theta_2$ may be approximately equal to an angle greater than about 0° and less than about 270°. In some instances, the first angle $\theta_1$ may be equal to the second angle $\theta_2$. As will be explained in the following disclosure, the selected angular orientation defined by the first angle $\theta_1$ and the second angle $\theta_2$ will allow an operator of the medical device assembly 10 to access otherwise obstructed or potentially difficult regions to be analyzed for determining a pain threshold of the patient P (e.g., the lateral walls of a pelvis).

In other examples, the first and second axes $A_{14}$-$A_{14}$, $A_{12}$-$A_{12}$ extending through each of the body $14_B$ of the algometer portion 14 and the tube-shaped body $12_B$ of the therapeusis delivery portion 12 may not axially deviate along their respective axes $A_{14}$-$A_{14}$, $A_{12}$-$A_{12}$. Because each of the body $14_B$ of the algometer portion 14 and the tube-shaped body $12_B$ of the therapeusis delivery portion 12 may not axially deviate along their respective axes $A_{14}$-$A_{14}$, $A_{12}$-$A_{12}$ (i.e., each of the first and second axes $A_{14}$-$A_{14}$, $A_{12}$-$A_{12}$ may remain substantially linear), the body $14_B$ of the algometer portion 14 and the tube-shaped body $12a$ of the therapeusis delivery portion 12 may remain parallel to one another.

The design of the algometer portion 14 and the therapeusis delivery portion 12 to include an angular deviation (if any) along their respective axes $A_{14}$-$A_{14}$, $A_{12}$-$A_{12}$ as described above may depend on the application of the medical device assembly 10. For example, if the medical device assembly 10 is to be utilized for determining pain and/or treating pain in a vaginal region of a patient P, the first angle $\theta_1$ and the second angle $\theta_2$ may be approximately equal to about 70°. In another example, if the medical device assembly 10 is utilized for endoscopically determining pain and/or treating pain of a patient P (by, e.g., disposing the force application sensor 26a against the patient's skin), the first angle $\theta_1$ and the second angle $\theta_2$ may be approximately equal to about 0°. In yet another example, if the medical device assembly 10 is utilized for superficially determining pain and/or treating pain of a patient P (by, e.g., disposing the force application sensor 26a against the patient's skin), the first angle $\theta_1$ and the second angle $\theta_2$ may be approximately equal to about 0°. In some instances, if the medical device assembly 10 is utilized in an ear-nose-throat (ENT) application for determining pain and/or treating pain of a patient P (by, e.g., disposing the force application sensor 26a against the larynx), the first angle $\theta_1$ and the second angle $\theta_2$ may be between approximately equal to about 0° and 45°. In another implementation, if the medical device assembly 10 is utilized in dental application for determining pain and/or treating pain of a patient P (e.g., by disposing the force application sensor 26a adjacent a patient's gums), the first angle $\theta_1$ and the second angle $\theta_2$ may be between approximately equal to about 0° and 270°.

Figure 5:
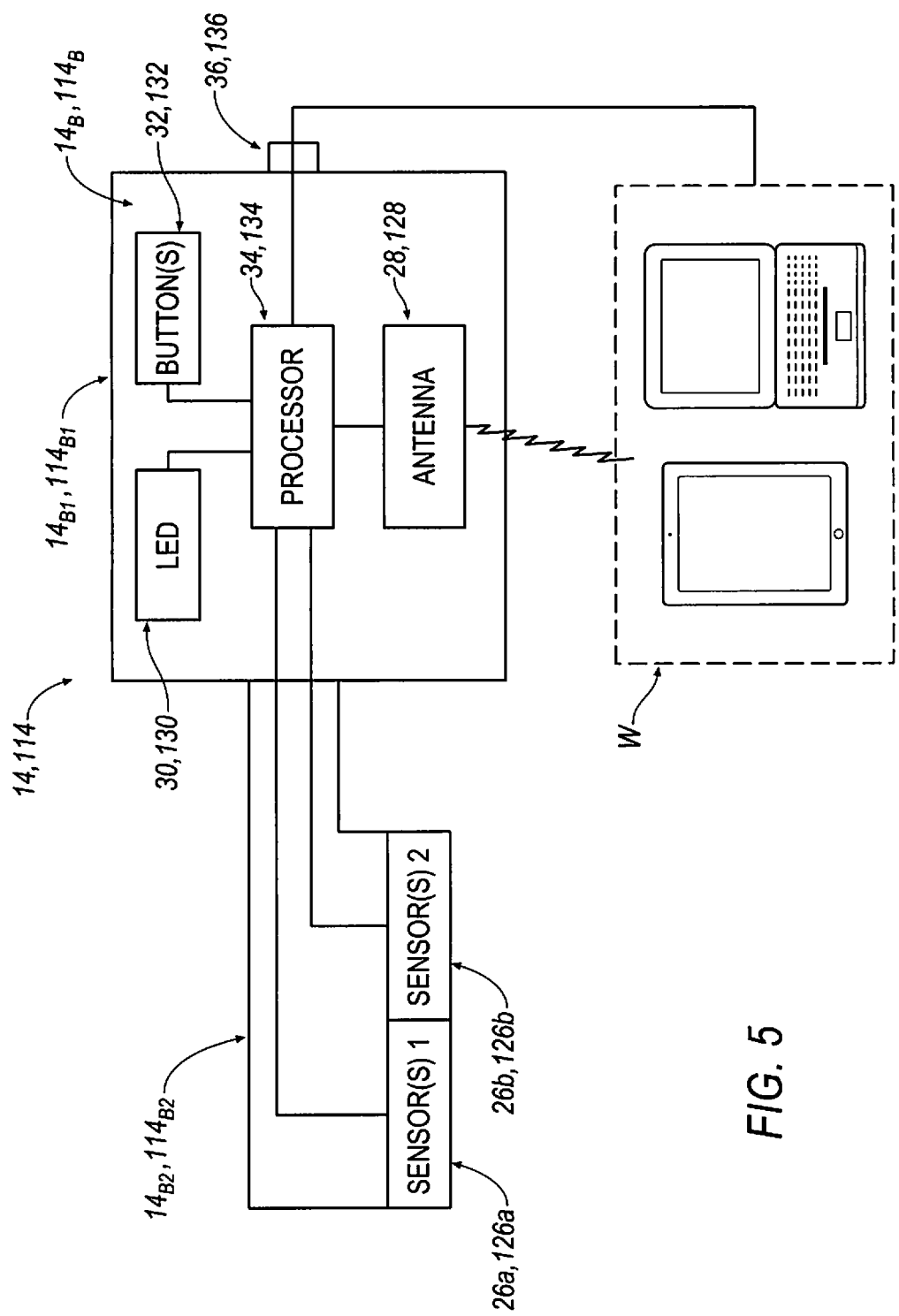
FIG. 5 is a block diagram of the medical device assembly of FIGS. 1A-1D or FIGS. 3A-3D.

Referring to FIG. 4, the force application sensor 26a may be disposed upon the distal end $14_D$ of the body $14_B$ of the algometer portion 14. With reference to FIG. 5, the force application sensor 26a may be hard-wired or wirelessly connected to electronics (e.g., a processor 34) disposed within, for example, the body $14_B$ of the algometer portion 14.

The force application sensor 26a may comprise a strain gauge or other component for measuring the application of force F in a small amount (e.g., 0.1 to 100 grams) that measures forces F directed to a surface of the patient P as a result of an operator of the medical device assembly 10: (1) gripping the handle portion $14_{B1}$ of the body $14_B$ of the algometer portion 14 and (2) pushing the force application sensor 26a toward the surface of the patient P. In some instances, the strain gauge may comprise a Ni—Cu Metal foil construction. In some implementations, the strain gauge may determine a range of input forces F between about 0N to 1N, 0N to 5N, or 0N to 10N. In some examples, the strain gauge may include the following dimensions: 720.639 mm in length, 10 microns in width and 0.05 microns in thickness. In some instances, the stain gauge may be defined by a resistance equal to approximately about 706.226 kΩ. In other examples, an exemplary strain gauge may be commercially available from Strain Measurement Devices under the name S256.

As seen in FIG. 5, the amount of force F applied to the surface of the patient P by the operator may be determined by the electronics (e.g., the processor 34) subsequently transmitted to for example, a computer workstation W such that the data may be visually represented upon, for example, a display or monitor of the computer workstation W for clinical analysis by the operator or another clinician. The force data may be transmitted from the processor 34 to the computer workstation W over a wired connection (by way of, e.g., a hardwire data port 36) or a wireless connection. In some implementations, a wired connection directly connects the processor 34 to the computer workstation W or a wireless connection (e.g., a Bluetooth connection) indirectly connects the electronics to the computer workstation W by way of, for example an antenna 28 disposed within the body $14_B$ of the algometer portion 14. The antenna 28 is connected to the processor 34.

The processor 34 may also be connected to an accelerometer (not shown) disposed within the body $14_B$ of the algometer portion 14 to allow for the storage of spatial coordinate positions of the medial device assembly 10 for allowing clinicians to determine the success or failure of previously-applied therapy to a previously-examined surface area of the patient P over a period of time. The force data could be recorded and saved in data collection software (e.g., MICROSOFT EXCEL®) of the computer workstation W. In some instances, any portion of the medical device assembly 10 may include, for example, indicia, lines, markings or the like in order to spatially assist the operator in determining, for example, depth of insertion of the medical device assembly 10 within a body cavity of the patient P.

The processor 34 may be connected to other components that may or may not be associated with the medical device assembly 10. In some instances, other components may include, for example: a battery, one or more light emitting diodes (LEDs) 30, a liquid crystal display (LCD), buttons 32 or the like. In an example, the LCD may display force values measured from the force application sensor 26a in order to permit, for example, a clinician to immediately visually determine an amount of force F being applied to a patient P by the algometer portion 14. In some instances, the one or more LEDs 30 may be illuminated when the medical device assembly 10 is powered on. In other examples, the one or more LEDs 30 may be illuminated when the processor 34 is paired with the computer workstation W for communicating force data thereto. In other examples, the one or more other components may also include the EMG sensor 26b that measures changes in nerve conduction or muscle spasms.

Other components connected to the electronics may include a battery disposed within the body $14_B$ of the algometer portion 14. The specifications of the battery may be dependent upon an overall power consumption of the medical device assembly 10. In some examples, power consumption considerations of the medical device assembly 10 may include: strain gauge bias voltage of the force application sensor 26a, Wheatstone bridge input voltage, the supply voltage of the one or more LEDs 30 and the like. The bias and input voltage of the sensor strain gauge and Wheatstone bridge may require approximately 3V to 5V.

The electronics may be at different potentials, which may require voltage steps (up/down) that may be addressed by a voltage regulator circuit connected to, for example, a single AAA battery with a 1.5V rating.

Upon the operator of the medical device assembly 10 pushing the force application sensor 26a toward the surface of the patient P and locating a specific spatial area of discomfort of the patient, the operator may (1) guide the flexible needle N through the tube-shaped body 12$_B$ of the therapeusis delivery portion 12 and (2) optionally arrange the flexible needle N for contact with the area of discomfort of the patient P. Then, the operator may actuate the syringe S for delivering therapeusis: (1) from the therapeusis container C, (2) through the flexible needle N and (3) into to the area of discomfort of the patient P for providing therapy to the patient P. The therapeusis contained by the therapeusis container C that is ultimately delivered to the area of discomfort of the patient P may include, for example, a pharmaceutical, anesthetic or the like. Although an exemplary embodiment described above is directed to an externally-located therapeusis container C containing the therapeusis, other implementations may include a therapeusis container C stowed within, for example, the algometer portion 14 such that a user may actuate, for example, a button 32 for causing therapeusis to be delivered from the therapeusis container C from the algometer portion 14 to the area of discomfort of the patient P. Furthermore, the therapeusis may be delivered without using a flexible needle N (e.g., the therapeusis may be pumped through the tube-shaped body 12$_B$ of the therapeusis delivery portion 12 for topical delivery to the area of discomfort of the patient P.

An exemplary amplification of the Wheatstone Bridge Output Voltage is now discussed. Micro-electro-mechanical-systems (MEMS) devices may have a supply voltage of up to 100V but only output a voltage on the order of microns (Froehlich, n.d.). Due to this low output, it may have a gain amplifier that will amplify the measurable quantity that the sensor outputs. The output voltage for the Wheatstone bridge in the pressure-sensing device should be amplified in order for the interface circuits to be able to properly measure the voltage. Typical microcontroller inputs operate with an input of 0-3.3 volts (Froehlich, n.d.). An applicable device that was chosen to amplify the bridge output voltage is an operational amplifier (op-amp). The configuration of the operational amplifier will be in the form of a non-inverting op-amp. The image below shows a non-inverting operational amplifier.

The fabrication of operational amplifiers makes it so that there is a very large input impendence on the input terminals of the device. As a result, the current going into these terminals are so small that their amounts are negligible. The input of this amplifier will be the output voltage of the bridge circuit of the pressure sensor. Below is the equation for the output of the non-inverting op-amp, in relation to the input voltage:

$$V_{out} = \left(1 + \frac{R_2}{R_1}\right) V_{in}. \quad \text{(Eq. 2)}$$

Looking at the above equation (Eq. 2), the gain of the amplifier, K, is $$1 + \frac{R_2}{R_1}.$$

The gain is dependent on the values of resistors $R_1$ and $R_2$. These resistors will be chosen such that the output voltage of the operational amplifier will be in an adequate range to be read by other electronics. This gain will be selected after the device is actually fabricated and the output voltage can actually be tested.

In order for the users to know how much force F is being applied to the force application sensor 26a, it may create a function that depends on the force F being applied. This function may be related to the applied force F of the amplified output voltage from the Wheatstone bridge. This will be done in the laboratory. A machine will apply many increments of known forces F to the force application sensor 26a and the corresponding output voltages from the bridge will be recorded. These data points will be plotted with output voltage on the y-axis and applied force F on the x-axis. After all of the data points have been collected software, such as MATLAB, will be used to realize the equation of the line from the data points.

Calibration of the force application sensor 26a may be done in order to ensure accurate voltage-to-force conversions. For example, if the Wheatstone bridge has an output voltage of 1 volt at equilibrium (when no force F is being applied), rather than zero, this 1 volt may correlate to no force F being applied to the force application sensor 26a.

In some implementations, the electronics may include Texas Instrument (TI) CP3SP33 Connectivity Processor with Cache, Digital Signal Processor (DSP), Bluetooth, USB and a dual Controller Area Network (CAN) Interface to provide the processing power of the interface. The TI DSP could be able to pair with its corresponding USB hub device. This will enable the transmitting and receiving functionality of the DSP. The chip could contain an analog to digital converter to take the diaphragm voltage signal from the sensor and convert it to force F. The force F could then be transmitted to the computer workstation (e.g., a paired laptop) and stored in a data file (TI, 2014).

Referring to FIGS. 3A-3D, an exemplary medical device assembly is shown generally at 100. The medical device assembly 100 includes a therapeusis delivery portion 112 (see also, FIGS. 3D', 3D'', 3D''') and an algometer portion 114. Each of the therapeusis delivery portion 112 and the algometer portion 114 includes a body 112$_B$, 114$_B$ having a proximal end 112$_P$, 114$_P$ and a distal end 112$_D$, 114$_D$.

Figure 3A:
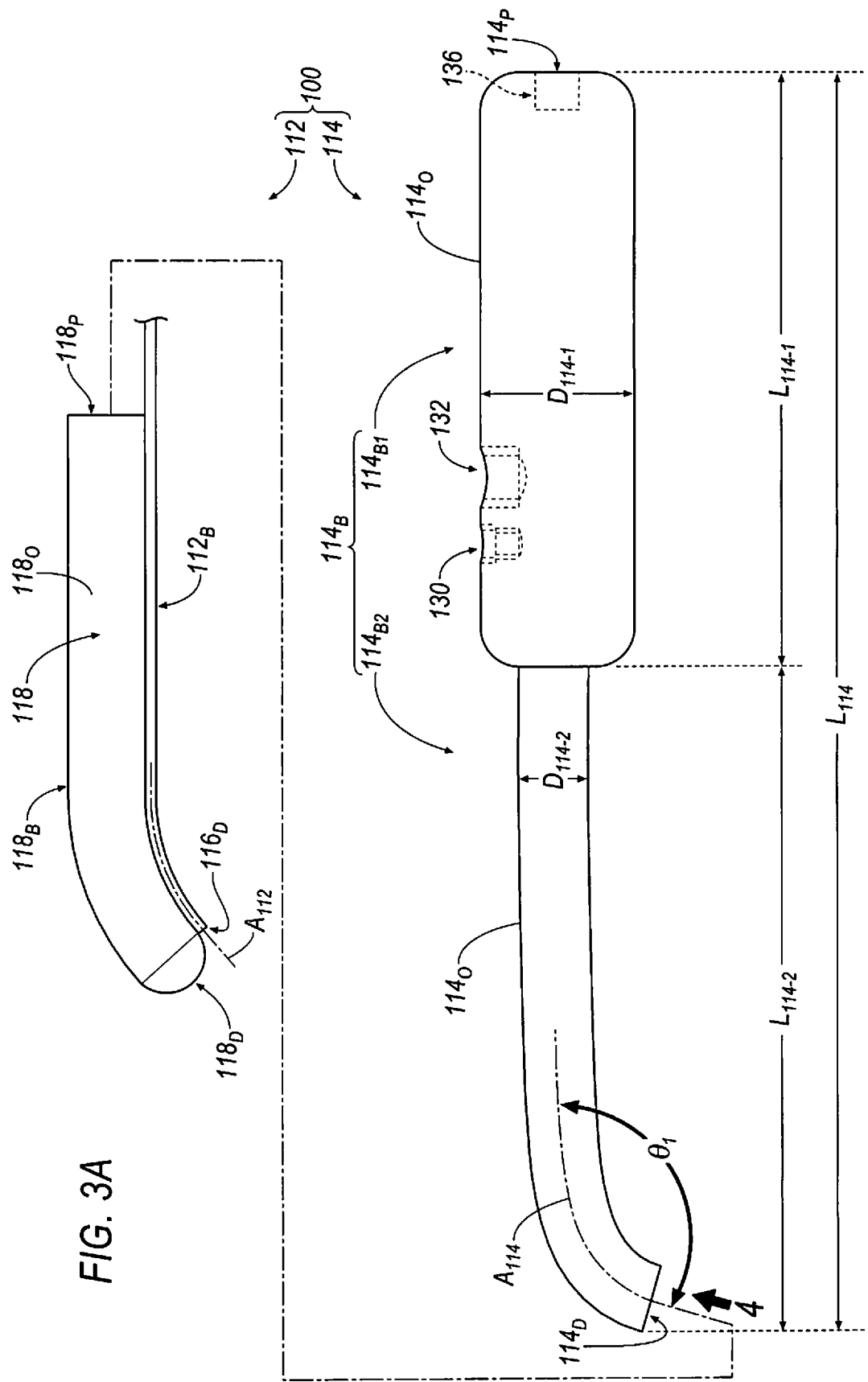
FIG. 3A is an exploded side view of an exemplary medical device assembly.
Figure 3B:
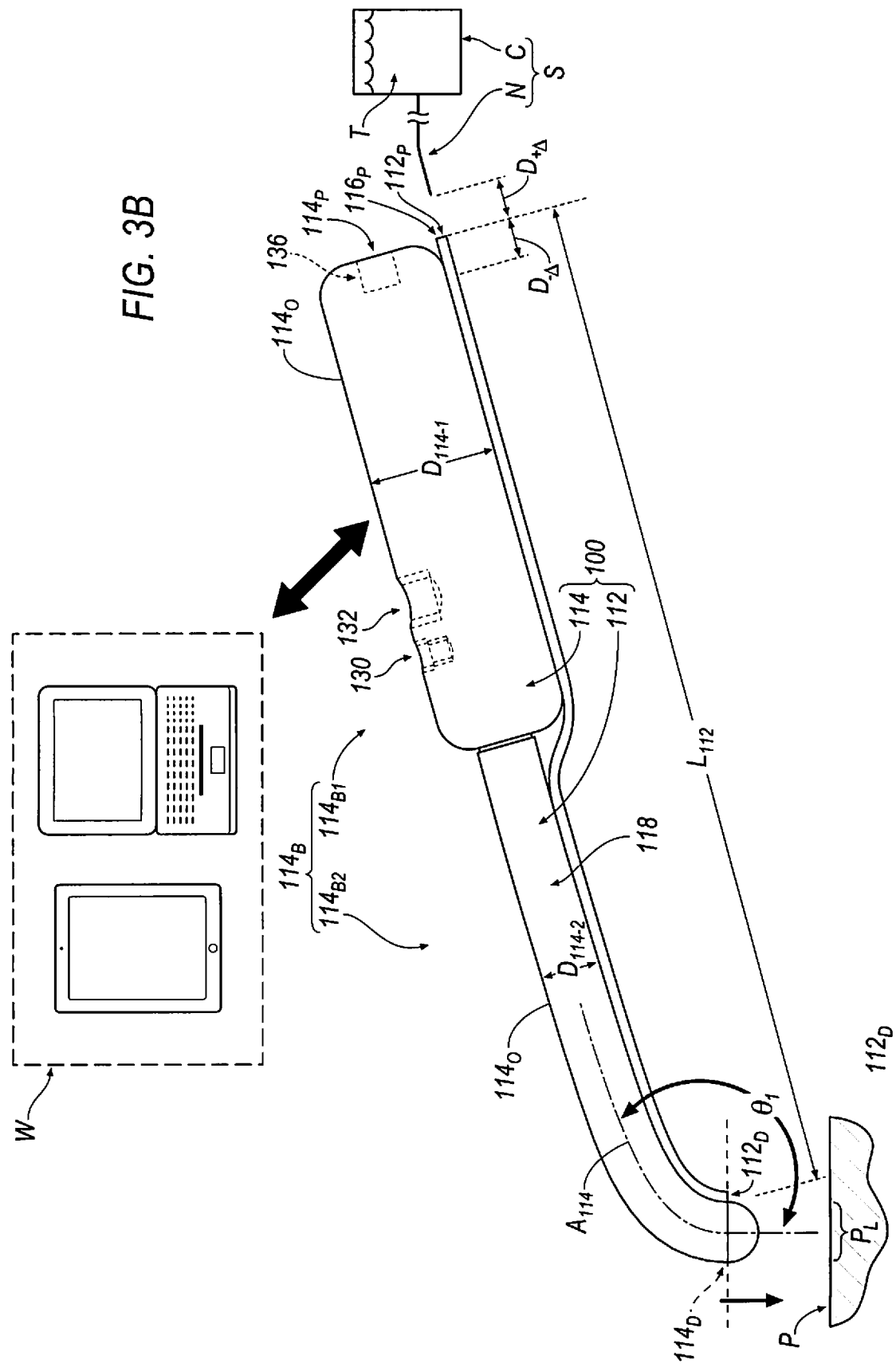
FIG. 3B is an assembled side view of the exemplary medical device assembly of FIG. 3A.

The body 112$_B$ of the therapeusis delivery portion 112 is similar to the body 12$_B$ of the therapeusis delivery portion 12 described above at FIGS. 1A-1D with the exception that the body 112$_B$ of the therapeusis delivery portion 112 is not attached to the algometer portion 114 with the one or more attachment clips 18. Rather, the body 112$_B$ of the therapeusis delivery portion 112 includes a sheath 118 that is sleeved-over a portion (e.g., the wand portion 114$_{B2}$) $L_{114-2}$ of a length $L_{114}$ of the body 114$_B$ of the algometer portion 114 that extends away from the distal end 114$_D$ of the body 114$_B$ of the algometer portion 114 as seen in FIGS. 3A-3B (i.e., the sheath 118 connects the body 112$_B$ of the therapeusis delivery portion 112 to the algometer portion 114). A remainder portion (e.g., the handle portion 114$_{B1}$) $L_{114-1}$ of the length $L_{114}$ of the body 114$_B$ of the algometer portion 114 may not be covered by the sheath 118.

The sheath 118 may be made substantially similar to a condom or prophylactic that promotes cleanliness or mitigates bacterial contamination of the portion $L_{114-2}$ of the length $L_{114}$ of the body 114$_B$ of the algometer portion 114. The sheath 118 may be made from any desirable material such as silicone, latex, plastic, any prophylactic material or the like. Although the sheath 118 may be made from one material (such as, e.g., a non-electrically-conductive material), the sheath 118 may include two or more materials. Exemplary examples of the sheath 118 including more than one material (e.g., a first, non-electrically-conductive material M1 and a second, electrically-conductive material M2) will be described in the following disclosure at FIGS. 3D', 3D", 3D'" whereby at least a portion of an enclosed distal end $118_D$ of the sheath 118 may optionally include the second, electrically-conductive material M2, e.g., a conductive thermoplastic polyurethane (such as Pre-Elect TPU 1511).

The sheath 118 generally includes a tube-shaped body $118_B$ having a proximal opening $118_P$ and an enclosed distal end $118_D$. The tube-shaped body $118_B$ includes an inner surface $118_I$ (see, e.g., FIGS. 3D', 3D", 3D'") and an outer surface $118_O$. The inner surface $118_I$ and the enclosed distal end $118_D$ define an axial algometer-receiving passage 120 (see, e.g., FIGS. 3D', 3D", 3D'") extending through the tube-shaped body $118_B$. Access to the axial algometer-receiving passage 120 is permitted by way of an axial opening formed by the proximal opening $118_P$ of the sheath 118.

As seen in FIGS. 3A-3B, the proximal opening $118_P$ of the sheath 118 is sized for receiving the distal end $114_D$ of the algometer portion 114 such that the wand portion $114_{B2}$ of the algometer portion 114 may be subsequently-disposed within the axial algometer-receiving passage 120 of the sheath 118 for forming the medical device assembly 100. Once the wand portion $114_{B2}$ of the algometer portion 114 is disposed within the axial algometer-receiving passage 120 of the sheath 118 as seen in FIG. 3B, the inner surface $118_I$ of sheath 118 defined by the enclosed distal end $118_D$ of the sheath 118 extends over and may be disposed adjacent the distal end $114_D$ of the body $114_B$ algometer portion 14 thereby creating a barrier (as seen in FIGS. 3D', 3D", 3D'") between the distal end $114_D$ of the body $114_B$ algometer portion 114 and the patient P.

Figure 3C:
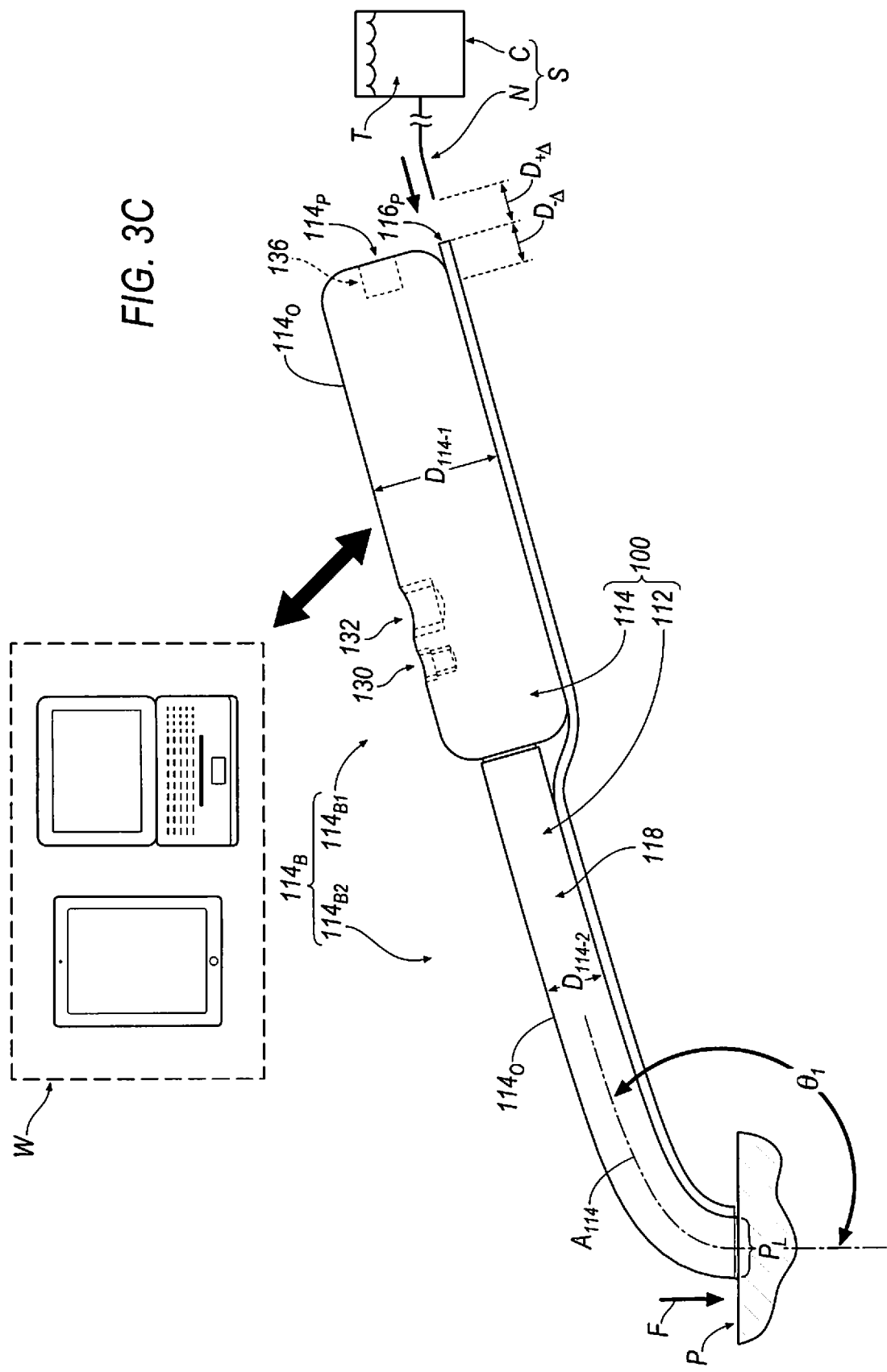
FIG. 3C is a side view of the medical device assembly of FIG. 3B disposed adjacent a patient.
Figure 3D:
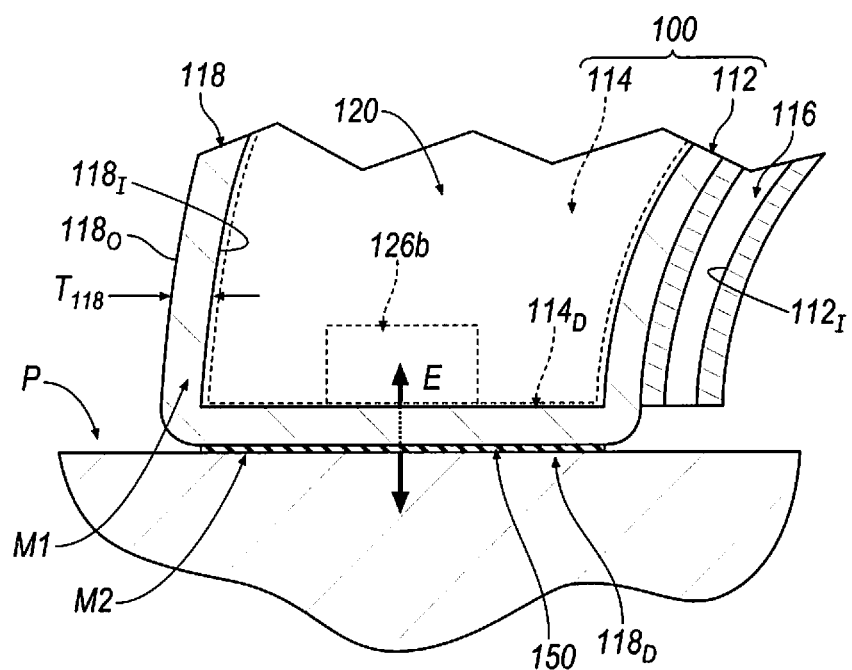
FIG. 3D is a side view of the medical device assembly of FIG. 3C showing therapeusis delivered to the patient by way of a needle extending through the medical device assembly that is interfaced with the patient.

With reference to FIGS. 3D', 3D", 3D'", in order to permit electrical communication between, for example, the patient P and an EMG sensor 126b located at the distal end $114_D$ of the algometer portion 114, at least a portion of the sheath 118 extending over the distal end $114_D$ of the body $114_B$ algometer portion 114 may include a second, electrically-conductive material M2 that is different from a first, non-electrically-conductive material M1; the second, electrically-conductive material M2 is shown generally at 150. Referring to FIG. 3D', a thickness $T_{118}$ of the portion of the sheath 118 extending over the distal end $114_D$ of the body $114_B$ algometer portion 114 may be impregnated with an electrically-conductive material 150 (such as, e.g., a conductive thermoplastic polyurethane) that permits communication of an electrical signal E from the patient P and through the thickness $T_{118}$ of the portion of the sheath 118 to the EMG sensor 126b. In another example, referring to FIG. 3D", the electrically-conductive material 150 (such as, e.g., a conductive thermoplastic polyurethane) may define an entirety of the thickness $T_{118}$ of the portion of the sheath 118 extending over the distal end $114_D$ of the body $114_B$ algometer portion 114 that permits communication of the electrical signal E from the patient P and through the thickness $T_{118}$ of the portion of the sheath 118 to the EMG sensor 126b. In yet another example, with reference to FIGS. 3D'", the outer surface $118_O$ of the portion of the sheath 118 extending over the distal end $114_D$ of the body $114_B$ algometer portion 114 may include a layer of electrically-conductive material 150 (such as, e.g., a conductive thermoplastic polyurethane) that is directly disposed adjacent the patient P and acts as a transmitter that communicates the electrical signal E through the thickness $T_{118}$ of the portion of the sheath 118 to a receiver, such as the EMG sensor 126b.

Referring to FIGS. 3A-3D, in addition to the sheath 118, the body 112a of the therapeusis delivery portion 112 may form a tube-shaped body having a therapeusis-delivering passage 116 (see, e.g., FIGS. 3D', 3D", 3D'") extending there-through. An inner surface $112_I$ (see, e.g., FIGS. 3D', 3D", 3D'") of the tube-shaped body $112_B$ defines the therapeusis-delivering passage 116.

The body $114_B$ of the algometer portion 114 includes the handle portion $114_{B1}$ and the wand portion $114_{B2}$. The handle portion $114_{B1}$ includes the proximal end $114_P$ of the algometer portion 114 and the wand portion $114_{B2}$ includes the distal end $114_D$ of the algometer portion 114. The handle portion $114_{B1}$ and the wand portion $114_{B2}$ may be respectively defined by a diameter $D^{114-1}$, $D_{114-2}$; the diameter $D^{114-1}$ of the handle portion $114_{B1}$ may be greater than the diameter $D_{114-2}$ of the wand portion $114_{B2}$.

As seen in FIGS. 3C-3D, the tube-shaped body $112_B$ of the therapeusis delivery portion 112 may define a therapeusis delivery port for delivering therapeusis T to a patient P. In order to deliver therapeusis to the patient P, a flexible needle N may be reciprocatingly-disposed within the therapeusis-delivering passage 116 extending through the body $112_B$ of the therapeusis delivery portion 112. The flexible needle N is interfaced with the patient P by: (1) inserting the flexible needle N through the a proximal opening $116_P$ (see, e.g., FIGS. 3B-3D) formed by the tube-shaped body $112_B$ of the therapeusis delivery portion 112 that is in fluid communication with the therapeusis-delivering passage 116, (2) extending the flexible needle N through the therapeusis-delivering passage 116 that extends along a length $L_{112}$ (see, e.g., FIG. 3B) of the tube-shaped body $112_B$ of the therapeusis delivery portion 112 and (3) extending the flexible needle N out of a distal opening $116_D$ formed by the tube-shaped body $112_B$ of the therapeusis delivery portion 112 that is in fluid communication with the therapeusis-delivering passage 116. The flexible needle N may be connected to a therapeusis container C that contains therapeusis.

In some implementations, the flexible needle N and therapeusis container C may be a conventional syringe S. In an example, one or more of the flexible needle N and the therapeusis container C may be directly interfaced with the medical device assembly 100. In other example, one or more of the flexible needled N and the therapeusis container C may not be directly interfaced (i.e., one or more of the flexible needle N and the therapeusis container may be 'indirectly' interfaced) with the medical device assembly 100 in, for example, a free-floating arrangement such that an operator holds, for example, one or both of the therapeusis delivery portion 112 and the algometer portion 114 with one hand and then the operator operates/holds flexible needle N and/or the therapeusis container C with his/her other hand. In an example, if the flexible needle N and the therapeusis container C form a syringe S, the syringe S may be interfaced with the therapeusis delivery portion 112 by way of, for example, a threaded connection (by way of, e.g., a Luer lock, not shown).

With reference to FIG. 4, in an example, one or more sensors 126 may be connected to the distal end $114_D$ of the algometer portion 114. A sensor 126a of the one or more sensors 126 may include a force application sensor for measuring an amount of force (according to the direction of arrow F as seen in, e.g., FIGS. 3C-3D) imparted by an operator from the handle portion $114_{B1}$ of the body $114_B$ of the algometer portion 114 to the distal end $114_D$ of the algometer portion 114. Another sensor 126b of the one or more sensors 126 may include a sensor that measures changes in nerve conduction or muscle spasms (e.g., an electro-myography (EMG) sensor).

Referring to FIGS. 3B-3C, in an example, prior to interfacing the flexible needle N with the medical device assembly 100, an operator disposes the force application sensor 126a adjacent a locus (e.g., a trigger-point) $P_L$ of a patient P (e.g., the levator ani muscles of the patient P) and applies an amount of force F thereto. During the course of applying the force application sensor 126a adjacent the locus $P_L$ of the levator ani muscles of the patient P, the operator may ask the patient P to describe the level of pain being experienced (e.g., on a zero-to-ten threshold with zero being no pain being experienced and ten being an extreme amount of pain being experienced). With reference to FIG. 3D, if, for example, the operator determines that the level of pain being described by the patient P is sufficient for providing therapeusis T to the locus $P_L$, the operator may then selectively interface the flexible needle N with the medical device assembly 100 as described above for communicating therapeusis T: (1) from the therapeusis container C, (2) through the flexible needle N, and (3) to or near the site of the locus $P_L$ where the patient P has described the level of pain being experienced.

At least a first portion of the body $114_B$ of the algometer portion 114 may axially extend along a first axis $A_{114}$-$A_{114}$, and, in some instances as seen in FIG. 3A, the tube-shaped body 112E of the therapeusis delivery portion 112 may axially extend along a second axis $A_{112}$-$A_{112}$; the first axis $A_{114}$-$A_{114}$ and the second axis $A_{112}$-$A_{112}$ may be parallel to one another. After the therapeusis delivery portion 112 is attached to the algometer portion 114 as described above at FIGS. 3A-3B, in some instances, the distal end $112_D$ of the tube-shaped body $112_B$ of the therapeusis delivery portion 112 may be aligned with the distal end $114_D$ of the body $114_B$ of the algometer portion 114. Further, the proximal end $112_P$ of the tube-shaped body 112a of the therapeusis delivery portion 112 may be arranged upstream of and extend beyond the proximal end $114_P$ of the body 1148 of the algometer portion 114 at a distance D+a. Alternatively, the proximal end $112_P$ of the tube-shaped body $112_B$ of the therapeusis delivery portion 112 may be arranged downstream of the proximal end $114_P$ of the body $114_B$ of the algometer portion 114 at a distance D-o (see, e.g., FIG. 3B).

As seen in FIGS. 3A-3D, in some instances, both of the first axis $A_{114}$-$A_{114}$ and the second axis $A_{112}$-$A_{112}$ may define a non-linear axial component. For example, a second portion of the body $114_B$ of the algometer portion 114 proximate the distal end $114_D$ of the body $114_B$ of the algometer portion 114 may axially deviate along an arcuate path to define a non-linear axial component of the first axis $A_{114}$-$A_{114}$; as a result of the non-linearity of the first axis $A_{114}$-$A_{114}$, the body $114_B$ of the algometer portion 114 may be defined to curve at a first angle $\theta_1$. Similarly, as seen in FIGS. 3A-3D, the tube-shaped body $112_B$ of the therapeusis delivery portion 112 proximate the distal end $112_D$ may axially deviate along an arcuate path to define a non-linear axial component of the second axis $A_{112}$-$A_{112}$; as a result of the non-linearity of the second axis $A_{112}$-$A_{112}$, the tube-shaped body $112_B$ of the therapeusis delivery portion 112 may be defined to curve at a second angle $\theta_2$. Each of the first angle $\theta_1$ and the second angle $\theta_2$ may be approximately equal to an angle greater than about 0° and less than about 270°. In some instances, the first angle $\theta_1$ may be equal to the second angle $\theta_2$. As will be explained in the following disclosure, the selected angular orientation defined by the first angle $\theta_1$ and the second angle $\theta_2$ will allow an operator of the medical device assembly 100 to access otherwise obstructed or potentially difficult regions to be analyzed for determining a pain threshold of the patient P (e.g., the lateral walls of a pelvis).

In other examples, the first and second axes $A_{114}$-$A_{114}$, $A_{112}$-$A_{112}$ extending through each of the body $114_B$ of the algometer portion 114 and the tube-shaped body $112_B$ of the therapeusis delivery portion 112 may not axially deviate along their respective axes $A_{114}$-$A_{114}$, $A_{112}$-$A_{112}$. Because each of the body $114_B$ of the algometer portion 114 and the tube-shaped body $112_B$ of the therapeusis delivery portion 112 may not axially deviate along their respective axes $A_{114}$-$A_{114}$, $A_{112}$-$A_{112}$ (i.e., each of the first and second axes $A_{114}$-$A_{114}$, $A_{112}$-$A_{112}$ may remain substantially linear), the body $114_B$ of the algometer portion 114 and the tube-shaped body $112_B$ of the therapeusis delivery portion 112 may remain parallel to one another.

The design of the algometer portion 114 and the therapeusis delivery portion 112 to include an angular deviation (if any) along their respective axes $A_{114}$-$A_{114}$, $A_{112}$-$A_{112}$ as described above may depend on the application of the medical device assembly 100. For example, if the medical device assembly 100 is to be utilized for determining pain and/or treating pain in a vaginal region of a patient P, the first angle $\theta_1$ and the second angle $\theta_2$ may be approximately equal to about 70°. In another example, if the medical device assembly 100 is utilized for endoscopically determining pain and/or treating pain of a patient P (by, e.g., disposing the force application sensor 126a against the patient's skin), the first angle $\theta_1$ and the second angle $\theta_2$ may be approximately equal to about 0°. In yet another example, if the medical device assembly 100 is utilized for superficially determining pain and/or treating pain of a patient P (by, e.g., disposing the force application sensor 126a against the patient's skin), the first angle $\theta_1$ and the second angle $\theta_2$ may be approximately equal to about 00. In some instances, if the medical device assembly 100 is utilized in an ear-nose-throat (ENT) application for determining pain and/or treating pain of a patient P (by, e.g., disposing the force application sensor 126a against the larynx), the first angle $\theta_1$ and the second angle $\theta_2$ may be between approximately equal to about 0° and 45°. In another implementation, if the medical device assembly 100 is utilized in dental application for determining pain and/or treating pain of a patient P (e.g., by disposing the force application sensor 126a adjacent a patient's gums), the first angle $\theta_1$ and the second angle $\theta_2$ may be between approximately equal to about 0° and 270°.

Referring to FIG. 4, the force application sensor 126a may be disposed upon the distal end $114_D$ of the body $114_B$ of the algometer portion 114. With reference to FIG. 5, the force application sensor 126a may be hard-wired or wirelessly connected to electronics (e.g., a processor 134) disposed within, for example, the body $114_B$ of the algometer portion 114.

The force application sensor 126a may comprise a strain gauge or other component for measuring the application of force F in a small amount (e.g., 0.1 to 100 grams) that measures forces F directed to a surface of the patient P as a result of an operator of the medical device assembly 100: (1) gripping the handle portion $114_{B1}$ of the body $114_B$ of the algometer portion 114 and (2) pushing the force application sensor 126a toward the surface of the patient P. In some instances, the strain gauge may comprise a Ni—Cu Metal foil construction. In some implementations, the strain gauge may determine a range of input forces F between about 0N to 1N, 0N to 5N, or 0N to 10N. In some examples, the strain gauge may include the following dimensions: 720.639 mm in length, 10 microns in width and 0.05 microns in thickness. In some instances, the stain gauge may be defined by a resistance equal to approximately about 706.226 kΩ. In other examples, an exemplary strain gauge may be commercially available from Strain Measurement Devices under the name S256.

With reference to FIG. 5, the amount of force F applied to the surface of the patient P by the operator may be determined by the electronics (e.g., the processor 134) subsequently transmitted to for example, a computer workstation W such that the data may be visually represented upon, for example, a display or monitor of the computer workstation W for clinical analysis by the operator or another clinician. The force data may be transmitted from the processor 134 to the computer workstation W over a wired connection (by way of, e.g., a hardwire data port 136) or a wireless connection. In some implementations, a wired connection directly connects the processor 134 to the computer workstation W or a wireless connection (e.g., a Bluetooth connection) indirectly connects the electronics to the computer workstation W by way of, for example an antenna 128 disposed within the body 114$_B$ of the algometer portion 114. The antenna 128 is connected to the processor 134.

The processor 134 may also be connected to an accelerometer (not shown) disposed within the body 114$_B$ of the algometer portion 114 to allow for the storage of spatial coordinate positions of the medial device assembly 100 for allowing clinicians to determine the success or failure of previously-applied therapy to a previously-examined surface area of the patient P over a period of time. The force data could be recorded and saved in data collection software (e.g., MICROSOFT EXCEL®) of the computer workstation W. In some instances, any portion of the medical device assembly 100 may include, for example, indicia, lines, markings or the like in order to spatially assist the operator in determining, for example, depth of insertion of the medical device assembly 10 within a body cavity of the patient P.

The processor 134 may be connected to other components that may or may not be associated with the medical device assembly 100. In some instances, other components may include, for example: a battery, one or more light emitting diodes (LEDs) 130, a liquid crystal display (LCD), buttons 132 or the like. In an example, the LCD may display force values measured from the force application sensor 126a in order to permit, for example, a clinician to immediately visually determine an amount of force F being applied to a patient P by the algometer portion 114. In some instances, the one or more LEDs 130 may be illuminated when the medical device assembly 100 is powered on. In other examples, the one or more LEDs 130 may be illuminated when the processor 134 is paired with the computer workstation W for communicating force data thereto. In other examples, the one or more other components may also include the EMG sensor 126b that measures changes in nerve conduction or muscle spasms.

Other components connected to the electronics may include a battery disposed within the body 114$_B$ of the algometer portion 114. The specifications of the battery may be dependent upon an overall power consumption of the medical device assembly 100. In some examples, power consumption considerations of the medical device assembly 100 may include: strain gauge bias voltage of the force application sensor 126a, Wheatstone bridge input voltage, the supply voltage of the one or more LEDs 130 and the like.

The bias and input voltage of the sensor strain gauge and Wheatstone bridge may require approximately 3V to 5V. The electronics may be at different potentials, which may require voltage steps (up/down) that may be addressed by a voltage regulator circuit connected to, for example, a single AAA battery with a 1.5V rating.

Upon the operator of the medical device assembly 100 pushing the force application sensor 126a toward the surface of the patient P and locating a specific spatial area of discomfort of the patient, the operator may (1) guide the flexible needle N through the tube-shaped body 112$_B$ of the therapeusis delivery portion 112 and (2) optionally arrange the flexible needle N for contact with the area of discomfort of the patient P. Then, the operator may actuate the syringe S for delivering therapeusis: (1) from the therapeusis container C, (2) through the flexible needle N and (3) into to the area of discomfort of the patient P for providing therapy to the patient P. The therapeusis contained by the therapeusis container C that is ultimately delivered to the area of discomfort of the patient P may include, for example, a pharmaceutical, anesthetic or the like. Although an exemplary embodiment described above is directed to an externally-located therapeusis container C containing the therapeusis, other implementations may include a therapeusis container C stowed within, for example, the algometer portion 114 such that a user may actuate, for example, a button 132 for causing therapeusis to be delivered from the therapeusis container C from the algometer portion 114 to the area of discomfort of the patient P. Furthermore, the therapeusis may be delivered without using a flexible needle N (e.g., the therapeusis may be pumped through the tube-shaped body 112$_B$ of the therapeusis delivery portion 112 for topical delivery to the area of discomfort of the patient P.

An exemplary amplification of the Wheatstone Bridge Output Voltage is now discussed. Micro-electro-mechanical-systems (MEMS) devices may have a supply voltage of up to 100V but only output a voltage on the order of microns (Froehlich, n.d.). Due to this low output, it may have a gain amplifier that will amplify the measurable quantity that the sensor outputs. The output voltage for the Wheatstone bridge in the pressure-sensing device should be amplified in order for the interface circuits to be able to properly measure the voltage. Typical microcontroller inputs operate with an input of 0-3.3 volts (Froehlich, n.d.). An applicable device that was chosen to amplify the bridge output voltage is an operational amplifier (op-amp). The configuration of the operational amplifier will be in the form of a non-inverting op-amp. The image below shows a non-inverting operational amplifier.

The fabrication of operational amplifiers makes it so that there is a very large input impendence on the input terminals of the device. As a result, the current going into these terminals are so small that their amounts are negligible. The input of this amplifier will be the output voltage of the bridge circuit of the pressure sensor. Below is the equation for the output of the non-inverting op-amp, in relation to the input voltage:

$$V_{out} = \left(1 + \frac{R_2}{R_1}\right) V_{in}. \quad \text{(Eq. 2)}$$

Looking at the above equation (Eq. 2), the gain of the amplifier, K, is $$1 + \frac{R_2}{R_1}.$$

The gain is dependent on the values of resistors $R_1$ and $R_2$. These resistors will be chosen such that the output voltage of the operational amplifier will be in an adequate range to be read by other electronics. This gain will be selected after the device is actually fabricated and the output voltage can actually be tested.

In order for the users to know how much force F is being applied to the force application sensor 126a, it may create a function that depends on the force F being applied. This function may be related to the applied force F of the amplified output voltage from the Wheatstone bridge. This will be done in the laboratory. A machine will apply many increments of known forces F to the force application sensor 126a and the corresponding output voltages from the bridge will be recorded. These data points will be plotted with output voltage on the y-axis and applied force F on the x-axis. After all of the data points have been collected software, such as MATLAB, will be used to realize the equation of the line from the data points.

Calibration of the force application sensor 126a may be done in order to ensure accurate voltage-to-force conversions. For example, if the Wheatstone bridge has an output voltage of 1 volt at equilibrium (when no force F is being applied), rather than zero, this 1 volt may correlate to no force F being applied to the force application sensor 126a.

In some implementations, the electronics may include Texas Instrument (TI) CP3SP33 Connectivity Processor with Cache, Digital Signal Processor (DSP), Bluetooth, USB and a dual Controller Area Network (CAN) Interface to provide the processing power of the interface. The TI DSP could be able to pair with its corresponding USB hub device. This will enable the transmitting and receiving functionality of the DSP. The chip could contain an analog to digital converter to take the diaphragm voltage signal from the sensor and convert it to force F. The force F could then be transmitted to the computer workstation (e.g., a paired laptop) and stored in a data file (TI, 2014).

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A medical device assembly, comprising:
a therapeusis delivery portion including a body having a proximal end and a distal end; and
an algometer portion including a body having a proximal end and a distal end,
wherein the body of the therapeusis delivery portion defines
a therapeusis-delivering passage and
an algometer-receiving passage, wherein the algometer-receiving passage is defined by an inner surface of the body of the therapeusis delivery portion, wherein the inner surface of the body of the therapeusis delivery portion extends from an opening in the proximal end of the body of the therapeusis delivery portion to the distal end of the body of the therapeusis delivery portion, and wherein the algometer-receiving passage is sized to receive a portion of the algometer portion for connecting the algometer portion to the therapeusis delivery portion.

2. The medical device assembly of claim 1, wherein the algometer portion includes:
a handle portion; and
a wand portion.

3. The medical device assembly of claim 2, wherein the body of the therapeusis delivery portion includes:
a sheath, wherein the sheath includes an inner surface and an outer surface, wherein the inner surface of the sheath defines the algometer-receiving passage.

4. The medical device assembly of claim 3, wherein the sheath includes a proximal opening and an enclosed distal end, wherein the proximal opening permits fluid communication with the algometer-receiving passage.

5. The medical device assembly of claim 4, wherein the body of the therapeusis delivery portion is defined by a substantially tube shape, wherein an inner surface of the body of the therapeusis delivery portion defines the therapeusis-delivering passage.

6. The portion of medical device assembly of claim 4, wherein at least a portion of the enclosed distal end of the sheath includes an electrically-conductive material.

7. The portion of medical device assembly of claim 4, wherein all of a thickness of the enclosed distal end of the sheath is formed from an electrically-conductive material.

8. The portion of medical device assembly claim 4, wherein a thickness of the enclosed distal end of the sheath is formed from a first material and a second material, wherein the first material is a non-conductive material, wherein the second material is an electrically-conductive material, wherein the electrically-conductive material is impregnated within the non-conductive material.

9. The portion of medical device assembly of claim 4, wherein a thickness of the enclosed distal end of the sheath is bound by the inner surface of the sheath and the outer surface of the sheath, wherein an electrically-conductive material is disposed adjacent the outer surface of the sheath along the enclosed distal end of the sheath.

10. The medical device assembly of claim 1 further including:
one or more sensors connected to the distal end of the algometer portion; and
a processor communicatively-coupled to the one or more sensors.

11. The medical device assembly of claim 10, wherein the processor is disposed within the body of the algometer portion.

12. The medical device assembly of claim 10, wherein the one or more sensors includes a force application sensor.

13. The medical device assembly of claim 12, wherein the one or more sensors includes an electromyography sensor.

14. The medical device assembly of claim 10 further comprising:
one or more visual indicators attached to the body of the algometer, wherein the one or more visual indicators includes at least one of a light emitting diode and a liquid crystal display.

15. The medical device assembly of claim 10 further comprising:
one or more user input devices attached to the body of the algometer portion.

16. A portion of a medical device assembly, comprising:
a therapeusis delivery portion including a body having a proximal end and a distal end, wherein the body of the therapeusis delivery portion defines a therapeusis-delivering passage and an algometer-receiving passage that is sized to receive a portion of an algometer portion of the medical device assembly, thereby connecting the algometer portion to the therapeusis delivery portion and forming the medical device assembly, wherein the body of the therapeusis delivery portion includes:
a sheath, wherein the sheath includes an inner surface and an outer surface, and
wherein the inner surface of the sheath defines the algometer-receiving passage and extends from an opening in the proximal end of the body of the therapeusis delivery portion to the distal end of the body of the therapeusis delivery portion.

17. The portion of the medical device assembly of claim 16, wherein the sheath includes a proximal opening and an enclosed distal end, wherein the proximal opening permits fluid communication with the algometer-receiving passage.

18. The portion of medical device assembly of claim 17, wherein at least a portion of the enclosed distal end of the sheath includes an electrically-conductive material.

19. The portion of medical device assembly of claim 17, wherein all of a thickness of the enclosed distal end of the sheath is formed from an electrically-conductive material.

20. The portion of the medical device assembly of claim 17, wherein a thickness of the enclosed distal end of the sheath is formed from a first material and a second material, wherein the first material is a non-conductive material, wherein the second material is an electrically-conductive material, wherein the electrically-conductive material is impregnated within the non-conductive material.

21. The portion of medical device assembly of claim 17, wherein a thickness of the enclosed distal end of the sheath is bound by the inner surface of the sheath and the outer surface of the sheath, wherein an electrically-conductive material is disposed adjacent the outer surface of the sheath along the enclosed distal end of the sheath.

22. A method, comprising:
disposing a force application sensor of an algometer portion of a medical device assembly according to claim 1 adjacent a locus of a patient;
determining a level of pain being experienced by the patient; and
providing therapy to the locus of the patient by communicating therapeusis:
from a therapeusis container,
through a needle, and
to the locus.

23. The method of claim 22, wherein prior to the disposing step, the method includes:
assembling the medical device by connecting the therapeusis portion to the algometer portion.

24. The method of claim 22, further comprising:
disposing one or more sensors connected to the distal end of the algometer portion adjacent the locus of the patient; and
obtaining data from the one or more sensors.

25. The method of claim 24, further comprising:
obtaining an amount of force applied to the locus of the patient.

26. The method of claim 23, further comprising:
obtaining a measurement related to changes in nerve conduction or muscle spasms at or near the locus of the patient.

* * * * *